(12) United States Patent
Lyons (10) Patent No.: US 8,394,100 B2
(45) Date of Patent: Mar. 12, 2013

(54) SURGICAL APPARATUS AND METHOD FOR MANIPULATING ONE OR MORE OSTEOCHONDRAL PLUGS

(75) Inventor: Chris M. Lyons, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1433 days.

(21) Appl. No.: 11/317,985

(22) Filed: Dec. 23, 2005

(65) Prior Publication Data

US 2007/0149982 A1 Jun. 28, 2007

(51) Int. Cl.
*A61B 17/16* (2006.01)

(52) U.S. Cl. ............................. 606/84; 606/99

(58) Field of Classification Search .................... 606/79, 606/99, 86 R, 88
See application file for complete search history.

(56) References Cited

U.S. PATENT DOCUMENTS

| | | | |
|---|---|---|---|
| 4,399,813 A * | 8/1983 | Barber | 606/99 |
| 5,919,196 A | 7/1999 | Bobic et al. | |
| 5,921,987 A | 7/1999 | Stone | |
| 5,964,805 A | 10/1999 | Stone | |
| 6,007,496 A | 12/1999 | Brannon | |
| 6,017,348 A * | 1/2000 | Hart et al. | 606/79 |
| 6,110,209 A | 8/2000 | Stone | |
| 6,306,142 B1 | 10/2001 | Johanson et al. | |
| 6,375,658 B1 | 4/2002 | Hangody et al. | |
| 6,395,011 B1 | 5/2002 | Johanson et al. | |
| 6,413,006 B1 * | 7/2002 | Neugart | 403/344 |
| 6,440,141 B1 | 8/2002 | Philippon | |
| 6,488,033 B1 | 12/2002 | Cerundolo | |
| 6,592,588 B1 | 7/2003 | Bobic et al. | |
| 6,622,731 B2 * | 9/2003 | Daniel et al. | 128/898 |
| 6,767,354 B2 * | 7/2004 | Johanson et al. | 606/179 |
| 6,852,114 B2 | 2/2005 | Cerundolo | |
| 6,855,115 B2 * | 2/2005 | Fonseca et al. | 600/488 |
| 7,611,540 B2 * | 11/2009 | Clifford et al. | 623/20.21 |
| 7,699,059 B2 * | 4/2010 | Fonseca et al. | 128/899 |
| 2004/0176771 A1 | 9/2004 | Schmieding | |
| 2004/0186576 A1 * | 9/2004 | Biscup et al. | 623/17.12 |
| 2004/0193154 A1 | 9/2004 | Leatherbury et al. | |
| 2005/0019748 A1 * | 1/2005 | Ochi et al. | 435/4 |
| 2005/0101962 A1 | 5/2005 | Schwenke et al. | |
| 2005/0222687 A1 | 10/2005 | Vunjak-Novakovic et al. | |
| 2006/0247790 A1 * | 11/2006 | McKay | 623/23.44 |

OTHER PUBLICATIONS

U.S. Appl. No. 11/340,024, filed Jan. 26, 2006, Nycz, et al.
U.S. Appl. No. 11/339,194, filed Jan. 25, 2006, Nycz, et al.
U.S. Appl. No. 11/338,926, filed Jan. 25, 2006, Bharadwaj, et al.
U.S. Appl. No. 11/340,884, filed Jan. 27, 2006, Shimko, et al.
U.S. Appl. No. 11/343,156, filed Jan. 30, 2006, Bharadwaj, et al.
U.S. Appl. No. 11/339,694, filed Jan. 25, 2006, Gil.

* cited by examiner

*Primary Examiner* — Ellen C Hammond (74) *Attorney, Agent, or Firm* — Sorell, Lenna and Schmidt LLP (57) ABSTRACT

An surgical apparatus and method are described for manipulating one or more osteochondral plugs, including, but not limited to, extracting and/or impacting the one or more osteochondral plugs.

15 Claims, 7 Drawing Sheets

SURGICAL APPARATUS AND METHOD FOR MANIPULATING ONE OR MORE OSTEOCHONDRAL PLUGS

BACKGROUND

The present disclosure relates to osteochondral implants or plugs and, more particularly, to a surgical apparatus and method for manipulating one or more osteochondral plugs, including, but not limited to, extracting and/or impacting the one or more osteochondral plugs.

Osteochondral plugs may be extracted from, and/or impacted into, various locations in the human body. For example, one or more osteochondral plugs may be impacted into the knee of the human body. More particularly, in the human body, the knee consists of three bones—a femur, a tibia, and a patella—that are held in place by various ligaments. The chondral surfaces of the femur and the tibia form a hinge joint, and the patella protects the joint. Portions of the chondral surfaces of the femur and the tibia, as well as the underside of the patella, are covered with an articular cartilage which allow the femur and the tibia to smoothly glide against each other without causing damage. A menicus sits between the articular cartilage and the bone to distribute weight and to improve the stability of the joint. The articular cartilage often tears, usually due to traumatic injury (often seen in athletics) and degenerative processes (seen in older patients). This tearing does not heal well due to the lack of nerves, blood vessels and lymphatic systems and the resultant knee pain and swelling and limited motion of the bone(s) and must be addressed.

Damaged adult cartilage has historically been treated by a variety of surgical interventions including lavage, arthroscopic debridement, and repair stimulation, all of which provide less than optimum results. Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" has been used to repair articular cartilage. This procedure involves removing injured tissue from the articular defect and drilling openings such as, for example, cylindrical holes in the base of the defect and underlying bone. Osteochondral plugs such as, for example, cylindrically shaped osteochondral plugs of healthy cartilage and bone, are obtained from another area of the patient, typically from a lower-bearing region of the joint under repair, or from a donor patient, and are implanted in the drilled holes. (The term "autograft" refers to tissue or cells which originate with or are derived from the recipient, whereas the term "allograft" refers to cells and tissue which originate with, or are derived from, a donor of the same species as the recipient, in this case, another human.)

However, one or more problems or issues may arise in connection with an osteochondral transplantation procedure. For example, multiple instruments may be required during the osteochondral transplantation, with one or more instruments being used for each step in the procedure, thereby possibly increasing the time spent during, and the overall costs and/or complexity of, the procedure. Moreover, in procedures involving multiple osteochondral plugs, the one or more sites containing healthy bone and cartilage may need to be revisited several times, from the articular defect, in order to complete the transplantation, thereby also possibly increasing the time spent during, and the overall costs and/or complexity of, the procedure. Also, during the impacting of one or more osteochondral plugs, the operator may not be able to adequately determine the amount of force that is being applied to each of the osteochondral plugs, and therefore may not be able to know whether enough force has been applied to suitably impact each of the osteochondral plugs, or whether too great a force is being applied against the osteochondral plugs during the impacting.

In view of all of the above and/or other considerations, what is needed is an apparatus and/or method for manipulating one or more osteochondral plugs, including, but not limited to, extracting and/or implanting the one or more osteochondral plugs, that overcomes one or more of the above-described problems, among other problems.

SUMMARY

According to an embodiment, a surgical method is provided that includes positioning a first osteochondral plug within a tubular member, positioning at least one other osteochondral plug within the tubular member, and impacting the at least one other osteochondral plug into a defect site. According to another embodiment, a surgical method is provided that includes positioning at least one osteochondral plug within a tubular member and coupling a pressure sensor to the at least one osteochondral plug. According to another embodiment, a surgical apparatus is provided that includes a tubular member defining a longitudinal passage wherein at least one osteochondral plug is adapted to be positioned within the longitudinal passage, and a pressure sensor adapted to be coupled to the at least one osteochondral plug so that the at least one osteochondral plug and the pressure sensor are positioned within the longitudinal passage of the tubular member at the same time. According to another embodiment, a surgical apparatus is provided that includes a tubular member sized to receive and hold in place a first osteochondral plug and at least one other osteochondral plug, and a protrusion adapted to be received by the tubular member.

Various embodiments of the invention may possess one or more of the above features and advantages, or provide one or more solutions to the above problems existing in the prior art, among other problems.

DETAILED DESCRIPTION

Figure 1A:
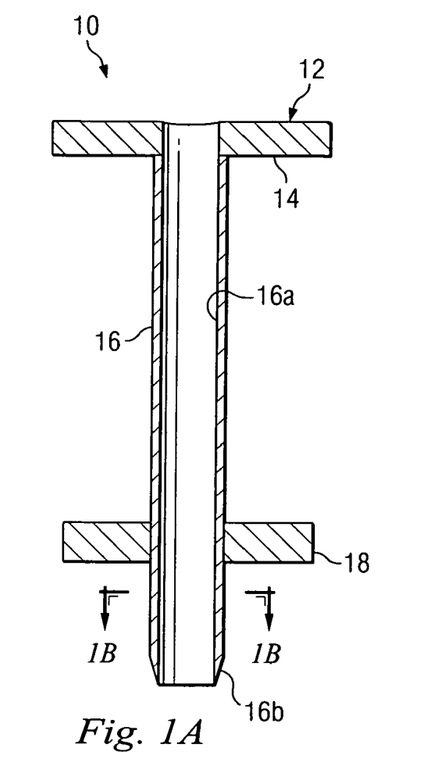
FIG. 1A is a sectional view of an apparatus according to an embodiment and including a cannula according to an embodiment.
Figures 1B, 2:
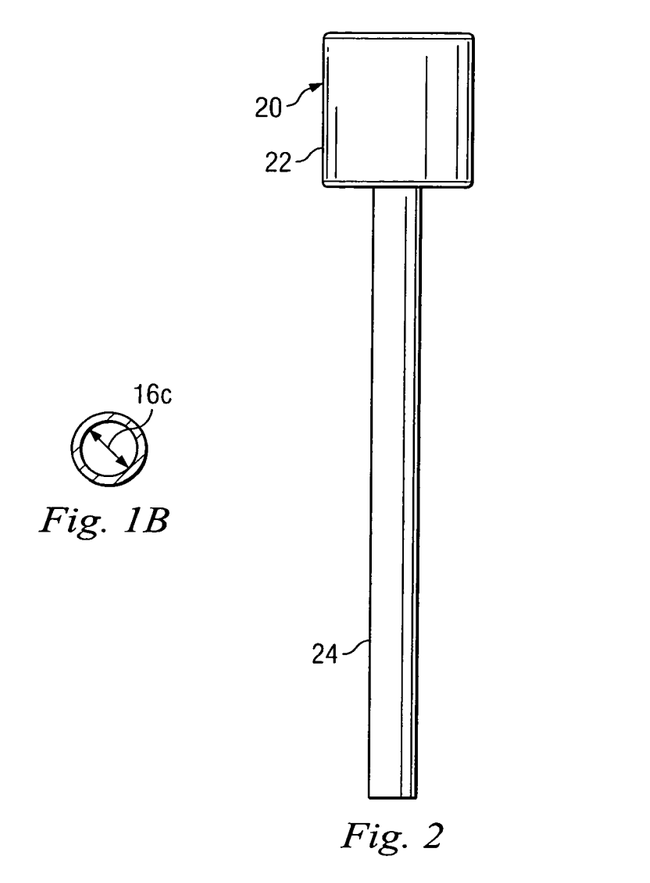
FIG. 1B is a sectional view of the cannula of FIG. 1 taken along line 1B-1B.
FIG. 2 is an elevational view of a pusher device according to an embodiment and adapted to be received by the cannula depicted in FIGS. 1A and 1B.

Referring to FIGS. 1A and 1B, a surgical apparatus is generally referred to by the reference numeral 10 and includes a cannula 12 having a handle 14 and a generally transparent tubular member 16 extending therefrom. The tubular member 16 defines a longitudinal passage 16a, and includes a tapered distal end portion 16b and a circular cross-section defining an inside diameter 16c. A stop 18 is movably coupled to the tubular member 16 of the cannula 12, and is adapted to translate longitudinally, relative to the tubular member 16 and for reasons to be described.

Referring to FIG. 2, the apparatus 10 further includes a pusher device 20 having a gripping or handle portion 22 and a protrusion 24 extending therefrom, which is adapted to be received by the tubular member 16 and extend within the passage 16a for reasons to be described. In an exemplary embodiment, the pusher device 20 may be in the form of an obturator.

Figure 3A:
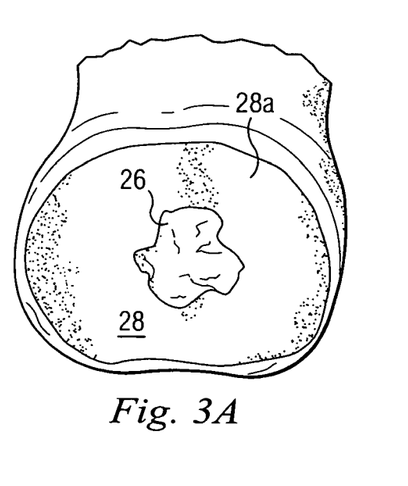
FIGS. 3A, 3B, 3C and 3D are top plan views depicting the preparation of an articular cartilage defect site.

In operation, the apparatus 10 may be used to, inter alia, extract one or more osteochondral plugs from donor bone and/or cartilage, and/or impact the one or more osteochondral plugs into, for example, an articular cartilage defect site to at least partially repair the articular cartilage, as described below. In an exemplary embodiment, as illustrated in FIGS. 3A, 3B, 3C and 3D, an articular cartilage defect site is prepared before the one or more osteochondral plugs are impacted into the articular cartilage defect site. Referring to FIG. 3A, a defect area such as, for example, a cartilage defect area 26 is present in bone and/or cartilage such as, for example, in articular cartilage 28 having a top surface 28a. In an exemplary embodiment, the articular cartilage 28 may be on, for example, the lateral femoral condyle of a human knee, any chondral surface on the femur, tibia and/or patella of a human knee, and/or on any other chondral and/or bone surface in the human body.

Figure 3B:
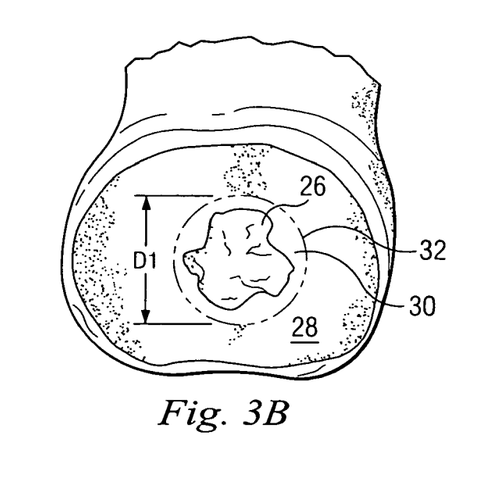

Referring to FIG. 3B, a diameter D1 of a defect site 30 is determined in response to determining the size of the cartilage defect area 26. In an exemplary embodiment, the size of the diameter D1 may be determined by, for example, determining a diameter of a circle 32 suitable to circumscribe the cartilage defect area 26 and sizing the diameter D1 to be at least as great as the diameter of the circle.

Figure 3C:
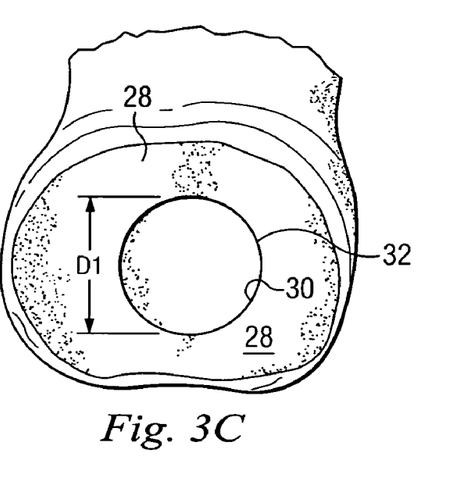
Figure 3D:
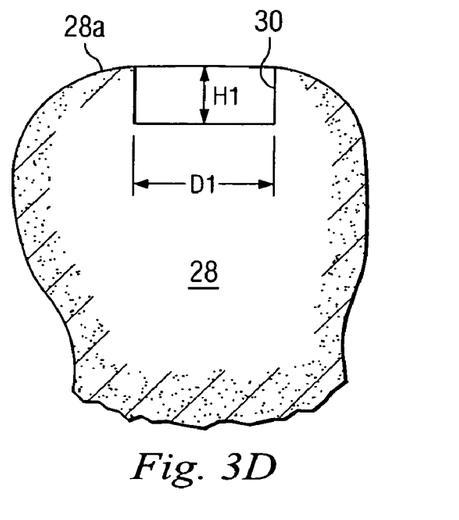

Referring to FIGS. 3C and 3D, the defect site 30 is prepared in a conventional manner using one or more defect debridement devices and/or defect debridement techniques, procedures and/or methods. As a result, and in an exemplary embodiment, the defect site 30 is in the form of a generally cylindrically-shaped blind bore in the articular cartilage 28, having the diameter D1 and defining a depth or height H1 from the top surface 28a of the articular cartilage.

Figure 4A:
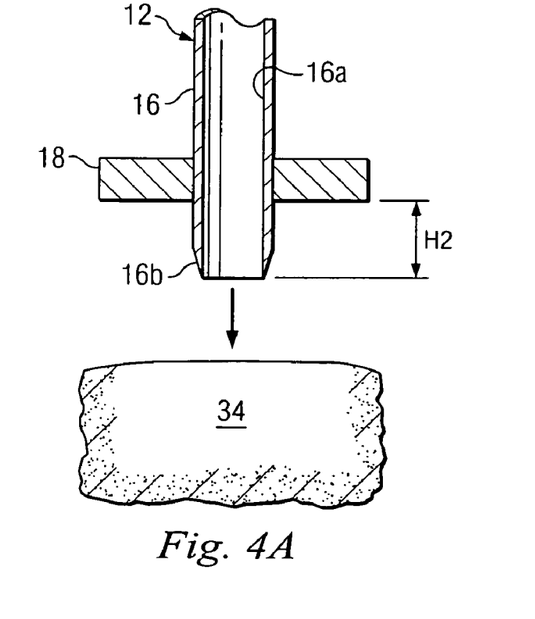
FIGS. 4A, 4B, 4C, 4D, 4E and 4F are sectional views depicting the extraction of osteochondral plugs from respective donor sites using the apparatus of FIGS. 1A and 1B.
Figure 4B:
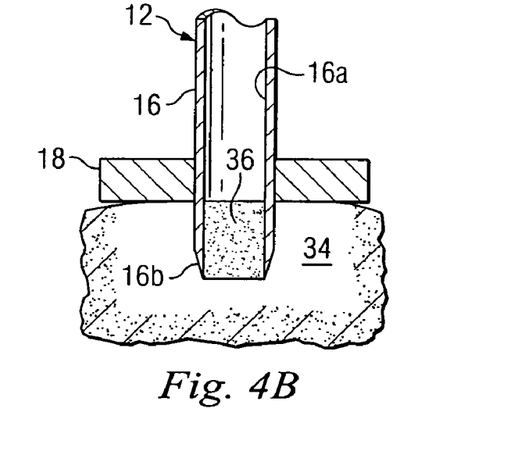

In an exemplary embodiment, as illustrated in FIGS. 4A, 4B, 4C, 4D, 4E and 4F, the one or more osteochondral plugs are extracted from donor bone and/or cartilage before the one or more osteochondral plugs are impacted into the defect site 30. Referring to FIGS. 4A and 4B, the stop 18 may be adjusted and moved either upwards or downwards, relative to the tubular member 16, so that a distance or height H2 is defined between the distal end of the tubular member 16 and the stop 18.

In an exemplary embodiment, the height H2 may be substantially equal to the height H1 defined by the defect site 30, and the stop 18 may be adjusted and the height H2 may be set by inserting the tubular member 16 into the defect area 30 so that the distal end of the tubular member 16 contacts the bottom surface of the defect area. The stop 18 may then be adjusted downwards until the stop 18 contacts the surface 28a of the articular cartilage 28, thereby causing the height H2 to be substantially equal to the height H1.

After the stop 18 has been adjusted relative to the tubular member 16, the position of the stop 18 is fixed relative to the tubular member 16. The stop 18 may be fixed in a wide variety of manners such as, for example, by using one or more set screws to set the stop 18 against the tubular member 16, and/or by using one or more clamps to engage both the stop 18 and the tubular member 16. In an exemplary embodiment, the stop 18 may be in the form of an adjustable clamp that extends about the tubular member 16, and the clamping force of the stop 18 against the tubular member 16 may be increased to fix the stop 18 to the tubular member 16 by, for example, tightening one or more fasteners.

After the position of the stop 18 has been fixed relative the tubular member 16, the cannula 12 is driven downwards into a donor site 34, which is composed of donor bone and/or cartilage, and the tubular member 16 is punched into the donor site 34. The tapered distal end portion 16b of the tubular member 16 facilitates the entrance and penetration of the tubular member 16 into the donor site 34. The tubular member 16 penetrates the donor site 34 until the stop 18 contacts the external surface of the donor site 34. As a result, the distal end of the tubular member 16 penetrates the donor site 34 to a depth substantially equal to the height H2. As another result, a portion of the donor site 34 is disposed within the passage 16a of the tubular member 16, thereby defining an osteochondral plug 36.

Figure 4C:
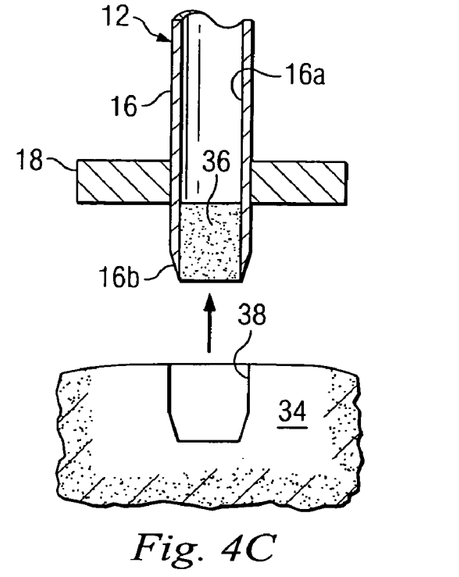

Referring to FIG. 4C, and after the osteochondral plug 36 has been defined, the cannula 12 is gently rocked back and forth so that the tubular member 16 rocks back and forth, causing the osteochondral plug 36 to separate from the remainder of the donor site 34. At this point, the cannula 12 is moved upwards so that the tubular member 16 moves upwards and away from the donor site 34. The osteochondral plug 36 remains positioned in the tubular member 16 and therefore is extracted from the donor site 34, moving upwards and away from the donor site 34. The cross-section of the osteochondral plug 36 generally corresponds to the cross-section of the tubular member 16, and the osteochondral plug 36 is generally cylindrically shaped, having a diameter substantially equal to the inside diameter 16c of the tubular member 16, and a height substantially equal to the height H2.

Due to its diameter and/or the material properties of bone and/or cartilage, of which the osteochondral plug 36 is composed, the osteochondral plug 36 fits snugly within the tubular member 16 and thus is prevented from sliding relative to, and exiting, the tubular member 16. The transparency of the tubular member 16 permits observance and inspection of the osteochondral plug 36 through the tubular member 16. As a result of the extraction of the osteochondral plug 36 from the donor site 34, an opening 38 is formed in the donor site 34.

Figure 4D:
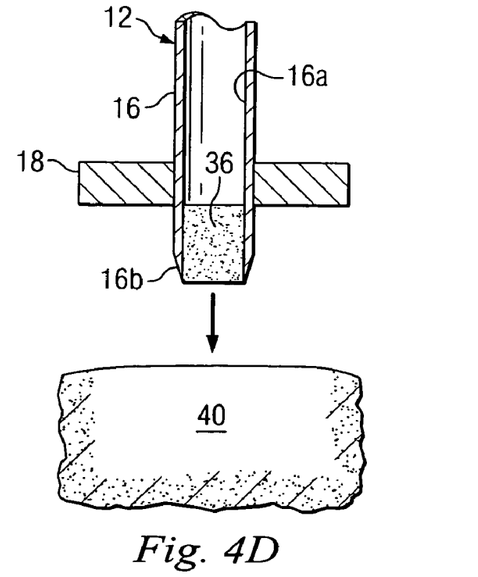
Figure 4E:
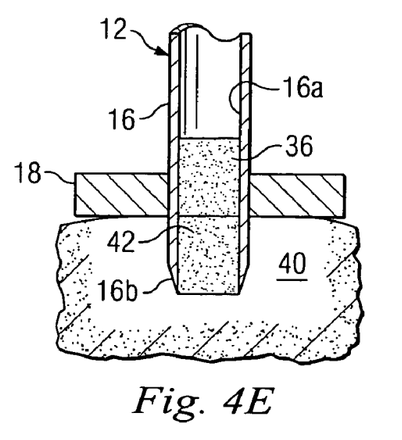

Referring to FIGS. 4D and 4E, the cannula 12 is again driven downwards into another donor site 40, which is composed of donor bone and/or cartilage and which may be adjacent to, or remote from, the donor site 34. The tubular member 16 is punched into the donor site 40, and the tapered distal end portion 16b of the tubular member 16 facilitates the entrance and penetration of the tubular member 16 into the donor site 40. The tubular member 16 penetrates the donor site 40 until the stop 18 contacts the external surface of the donor site 40. As a result, the distal end of the tubular member 16 penetrates the donor site 40 to a depth substantially equal to the height H2. As another result, a portion of the donor site 40 is disposed within the passage 16a, thereby defining an osteochondral plug 42. The disposal of the osteochondral plug 42 within the passage 16a forces the osteochondral plug 36 to slide upwards within the passage 16a. More particularly, one or more forces associated with punching the tubular member 16 into the donor site 40 are greater than and/or overcome the one or more frictional forces between the osteochondral plug 36 and the inside surface of the tubular member 16, thereby causing the osteochondral plug 36 to slide upwards within the passage 16a.

Figure 4F:
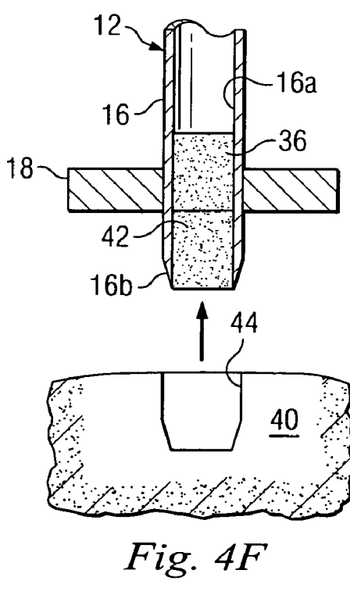

Referring to FIG. 4F, and after the osteochondral plug 42 has been defined, the cannula 12 is gently rocked back and forth so that the tubular member 16 rocks back and forth, causing the osteochondral plug 42 to separate from the remainder of the donor site 40. At this point, the cannula 12 is moved upwards so that the tubular member 16 moves upwards and away from the donor site 40. The osteochondral plug 42 remains positioned in the tubular member 16 and therefore is extracted from the donor site 40, moving upwards and away from the donor site 40. The osteochondral plug 42 is about the same size and shape as the osteochondral plug 36, being generally cylindrically shaped, having a diameter substantially equal to the inside diameter 16c of the tubular member 16, and having a height substantially equal to the height H2. Due to its diameter and/or the material properties of bone and/or cartilage, of which the osteochondral plug 42 is composed, the osteochondral plug 42 fits snugly within the tubular member 16 and thus is prevented from sliding relative to, and exiting, the tubular member 16. Moreover, the osteochondral plug 36 is adjacent to, and further abuts, the osteochondral plug 42. The osteochondral plug 36 is prevented from sliding relative to the tubular member 16 due to the presence of the osteochondral plug 42 in the tubular member 16, the diameter of the osteochondral plug 36 and/or the material properties of bone and/or cartilage, of which the osteochondral plug 36 is composed. The transparency of the tubular member 16 permits observance and inspection of the osteochondral plugs 36 and/or 42 through the tubular member 16. As a result of the extraction of the osteochondral plug 42 from the donor site 40, an opening 44 is formed in the donor site 40.

Figure 5:
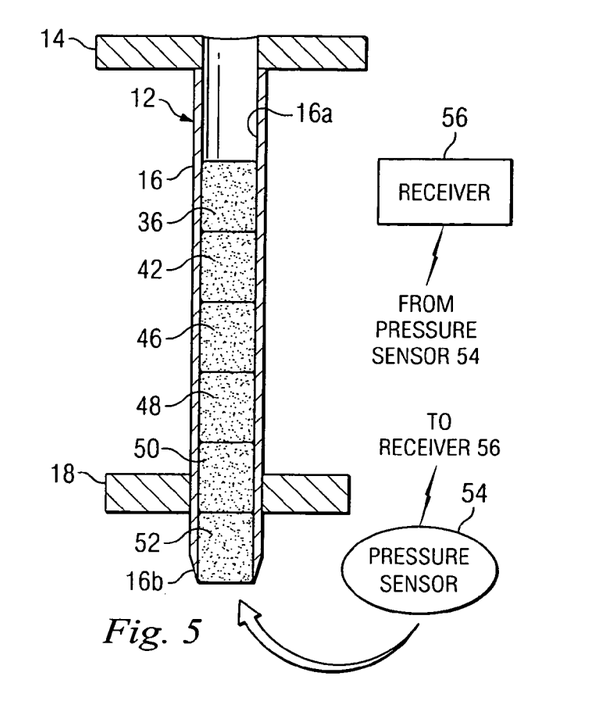
FIG. 5 is a partial sectional/partial diagrammatic view of the cannula of FIGS. 1A and 1B with a plurality of osteochondral plugs positioned in the cannula, and a sensor system adapted to be coupled to one of the osteochondral plugs.

Referring to FIG. 5, osteochondral plugs 46, 48, 50 and 52 are extracted from respective donor sites, and are positioned in the tubular member 16, in a manner substantially identical to the manner in which the osteochondral plugs 36 and 42 are extracted from the donor sites 34 and 40, respectively, and are positioned in the tubular member 16. As a result, and in an exemplary embodiment, the cannula 12 holds six osteochondral plugs. In an exemplary embodiment, the height H1, the height H2, and the height of each of the osteochondral plugs 46, 48, 50 and 52 may be about 15 mm. In an exemplary embodiment, the height H1, the height H2, and the height of each of the osteochondral plugs 46, 48, 50 and 52 may be less than, about or greater than 15 mm. The transparency of the tubular member 16 permits observance and inspection of the osteochondral plugs 36, 42, 46, 48, 50 and/or 52 through the tubular member 16.

After the osteochondral plugs 46, 48, 50 and 52 are extracted from respective donor sites, and are positioned in the tubular member 16, a pressure sensor 54 is coupled to the osteochondral plug 52. In an exemplary embodiment, the pressure sensor 54 includes a capacitor having a pair of spaced plates, and a resonant frequency of the pressure sensor 54 is dependent upon the spacing between the plates of the capacitor. The pressure sensor 54 is in communication with a receiver 56. In an exemplary embodiment, the pressure sensor 54 is in wireless communication with the receiver 56. In several exemplary embodiments, the pressure sensor 54 may be in the form of one or more of the pressure sensors disclosed in U.S. Pat. No. 6,855,115, the disclosure of which is incorporated herein by reference, or in any combination thereof. In an exemplary embodiment, the pressure sensor 54 may be coupled to the osteochondral plug 52 by, for example, being disposed in the interior of the osteochondral plug 52. In an exemplary embodiment, the pressure sensor 54 may be delivered into the interior of the osteochondral plug 52 via, for example, the distal end of a delivery catheter. In several exemplary embodiments, the pressure sensor 54 may be delivered into the interior of the osteochondral plug 52 via one or more of the delivery techniques, procedures and/or methods disclosed in U.S. Pat. No. 6,855,115, the disclosure of which is incorporated herein by reference.

Figure 6A:
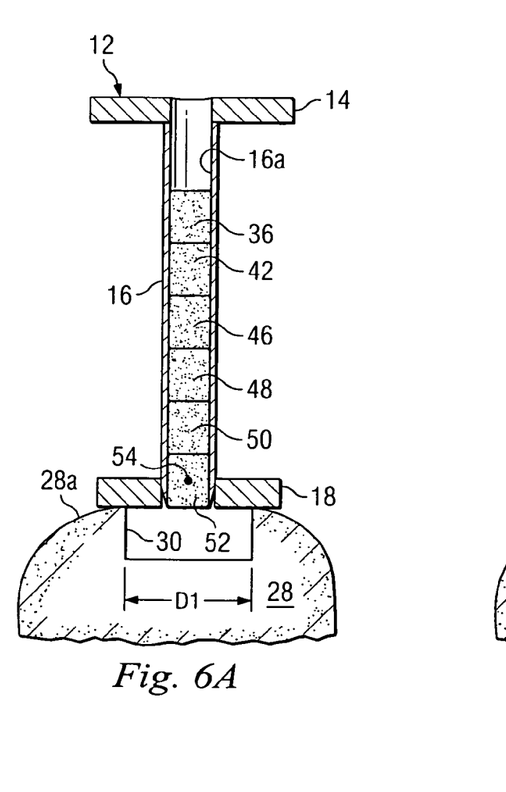
FIGS. 6A, 6B, 6C, 6D, 6E and 6F are sectional views depicting the impacting of the osteochondral plugs of FIG. 5 into the articular cartilage defect site of FIGS. 3A, 3B, 3C and 3D, using the apparatus of FIGS. 1A and 1B.

In an exemplary embodiment, the osteochondral plugs 36, 42, 46, 48, 50 and 52 are impacted into the defect site 30. Referring to FIG. 6A, the stop 18 is adjusted so that a surface of the stop 18 is aligned with the distal end of the tubular member 16. After the pressure sensor 54 is coupled to the osteochondral plug 52, the cannula 12 is positioned so that the stop 18 contacts the top surface 28a of the articular cartilage 28, and so that the tubular member 16 is above the defect site 30.

Figure 6B:
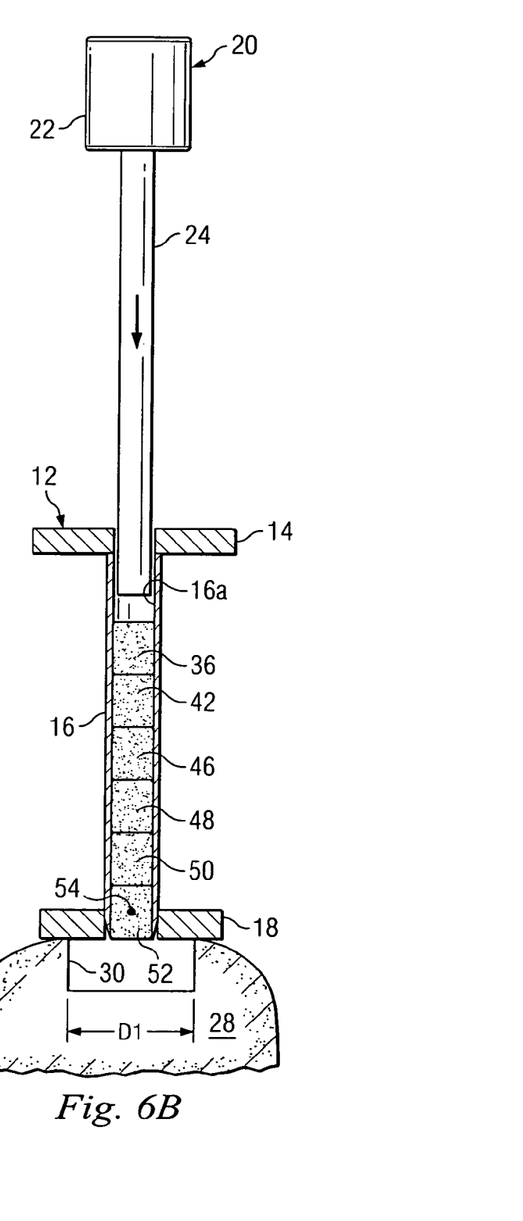
Figure 6C:
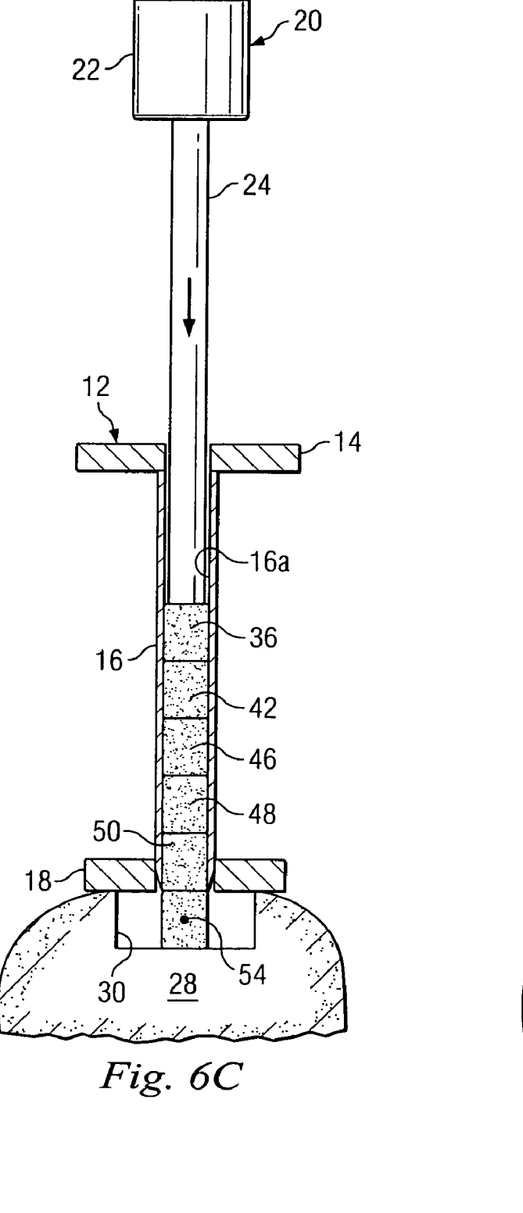

Referring to FIGS. 6B and 6C, the pusher device 20 is received by the tubular member 16 so that the protrusion 24 extends within the passage 16a of the tubular member 16. The handle portion 22 is gripped and the protrusion 24 is pushed downwards, as viewed in FIG. 6B, so that the distal end of the protrusion 24 contacts the osteochondral plug 36. The protrusion 24 is pushed further downward, causing a force to be applied against the osteochondral plug 36, which, in turn, applies a force against the osteochondral plug 42, which, in turn, applies a force against the osteochondral plug 46, which, in turn, applies a force against the osteochondral plug 48 which, in turn, applies a force against the osteochondral plug 50 which, in turn, applies a force against the osteochondral plug 52. As a result, the osteochondral plugs 36, 42, 46, 48, 50 and 52 all translate downwards in the passage 16a, and at least a portion of the osteochondral plug 52 exits the tubular member 16 and extends into the defect site 30. The protrusion 24 is pushed further downwards and, as a result, the osteochondral plug 52 entirely exits the tubular member 16 and is impacted into the defect site 30, as illustrated in FIG. 6C. In an exemplary embodiment, the osteochondral plug 52 may be impacted into the defect site 30 so that the osteochondral plug is positioned in about the middle of the defect site 30. The transparency of the tubular member 16 permits observance or inspection of the osteochondral plugs 36, 42, 46, 48, 50 and 52 in the tubular member 16 during the impacting of the osteochondral plug 52.

During the impacting of the osteochondral plug 52, the osteochondral plug 52 undergoes a pressure associated with, or in response to, the pushing of the protrusion 24 and the resulting application of a pushing force against the osteochondral plug 52 via the osteochondral plugs 36, 42, 46, 48 and 50. The pressure sensor 54 measures the amount of pressure that the osteochondral plug 52 undergoes during this force application. More particularly, the spacing between the plates of the above-described capacitor in the pressure sensor 54 changes in response to the application of the pushing force against the osteochondral plug 52 and, as a result, the resonant frequency of the pressure sensor 54 changes. The pressure sensor 54 sends one or more signals, one or more of which correspond to the change in resonant frequency of the pressure sensor 54, to the receiver 56. The receiver 56 receives the one or more signals and converts, conditions and/or processes the one or more signals to determine the amount of pressure that the osteochondral plug 52 is undergoing during its impacting into the defect site 30. In an exemplary embodiment, the receiver 56 outputs this pressure amount via, for example, a display screen. In response to an operator's reading of the pressure measurement provided by the pressure sensor 54, the force applied to the osteochondral plug 52 via the pusher device 20 may be increased, decreased or stopped altogether by increasing, decreasing or stopping altogether, respectively, the pushing force that the operator applies to the protrusion 24. As a result, the operator is able to adequately gage the amount of force that is being applied to the osteochondral plug 52 during its impacting, and may accordingly adjust the amount of applied force as needed and/or desired.

In several exemplary embodiments, the pressure sensor 54 may measure the amount of pressure that the osteochondral plug 52 is undergoing according to one or more of the techniques, procedures and/or methods disclosed in U.S. Pat. No. 6,855,115, the disclosure of which is incorporated herein by reference.

Figure 6D:
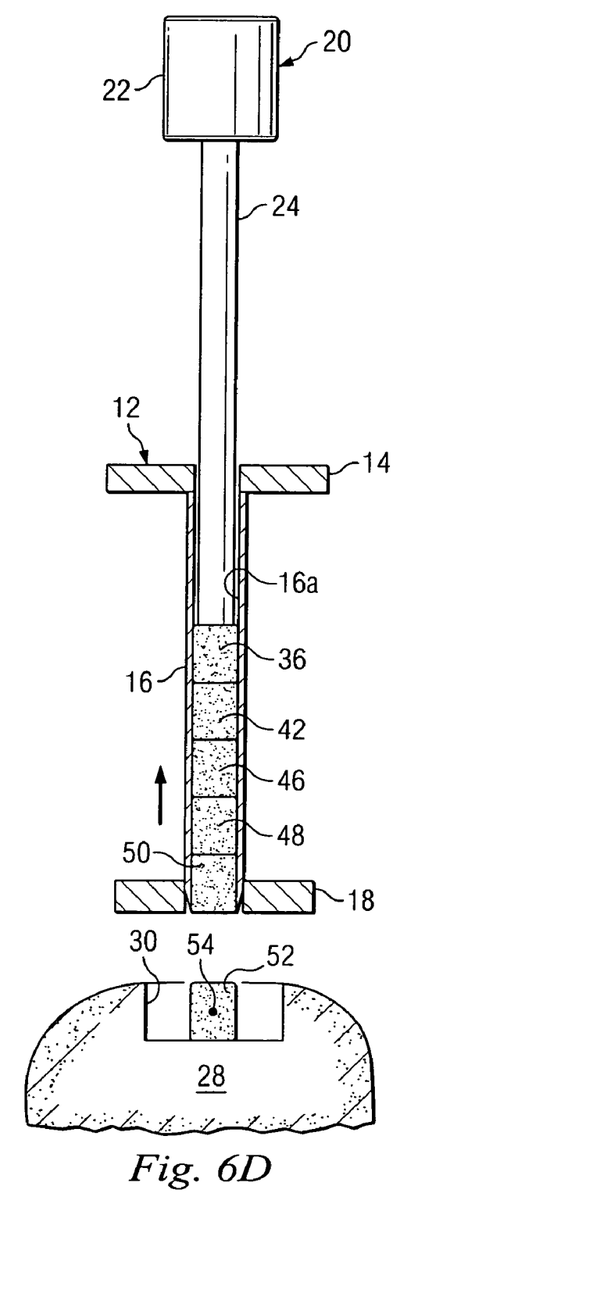

Referring to FIG. 6D, after the osteochondral plug 52 has been impacted into the defect site 30, the cannula 12 and the pusher device 20 are both lifted upwards and away from the defect site 30. During this movement, the osteochondral plugs 36, 42, 46, 48 and 50 remain positioned in the tubular member 16, but the protrusion 24 does not apply an appreciable force against the osteochondral plug 36. In an exemplary embodiment, after the osteochondral plug 52 has been impacted into the defect site 30, the protrusion 24 of the pusher device 20 may be removed from the passage 16a of the tubular member 16 of the cannula 12.

Figure 6E:
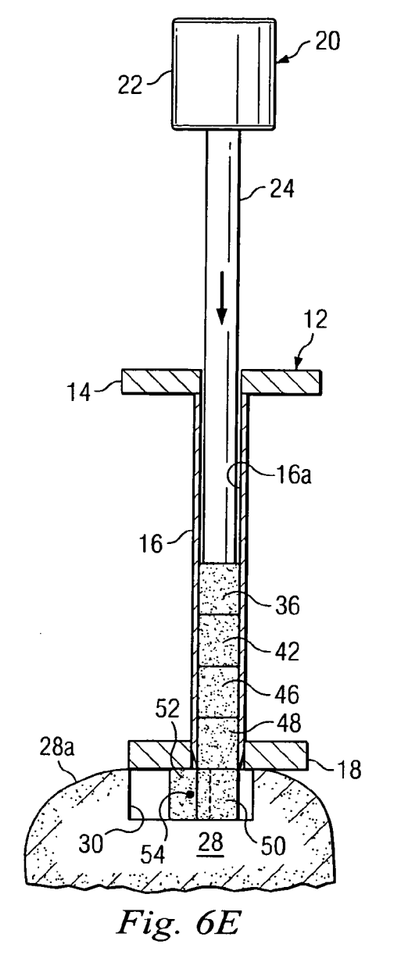

Referring to FIG. 6E, the cannula 12 and the pusher device 20 are repositioned, relative to the radial center of the defect site 30, and the protrusion 24 is again pushed downwards within the passage 16a of the tubular member 16 so that the distal end of the protrusion 24 contacts and applies another force against the osteochondral plug 36. The osteochondral plug 36, in turn, applies a force against the osteochondral plug 42, which, in turn, applies a force against the osteochondral plug 46, which, in turn, applies a force against the osteochondral plug 48 which, in turn, applies a force against the osteochondral plug 50. As a result, the osteochondral plugs 36, 42, 46, 48 and 50 all translate downwards in the passage 16a, and the osteochondral plug 50 exits the tubular member 16 and is impacted into the defect site 30, as illustrated in FIG. 6E. In an exemplary embodiment, the osteochondral plug 50 may be impacted into the defect site 30 so that the osteochondral plug 50 is positioned adjacent the osteochondral plug 52, contacting or nearly contacting the osteochondral plug 52. The transparency of the tubular member 16 permits observance or inspection of the osteochondral plugs 36, 42, 46, 48 and 50 in the tubular member 16 during the impacting of the osteochondral plug 50.

During the impacting of the osteochondral plug 50, the osteochondral plug 50 undergoes a pressure associated with, or in response to, the pushing of the protrusion 24 and the resulting application of a pushing force against the osteochondral plug 50 via the osteochondral plugs 36, 42, 46 and 48. The pressure sensor 54, which remains coupled to the osteochondral plug 52, measures the amount of pressure that the osteochondral plug 50 undergoes during this force application, at least with respect to when the osteochondral plug 50 extends in the defect site 30, in a manner substantially identical to the above-described manner in which the pressure sensor 54 measures the amount of pressure that the osteochondral plug 52 undergoes during the impacting of the osteochondral plug 52 into the defect site 30. The pressure sensor 54, which is disposed in the interior of the osteochondral plug 52, is able to measure the amount of pressure that the osteochondral plug 50 undergoes because of the one or more forces that propagate through the osteochondral plug 50, the osteochondral plug 52 and the defect site 30 in response to the application of the pushing force against the osteochondral plug 50. For example, one or more forces may be transferred from the osteochondral plug 50 to the osteochondral plug 52 because of the contact between the adjacent osteochondral plugs 50 and 52. In an exemplary embodiment, the radial range of pressure-amount detection by the pressure sensor 54 may be about 5 cm. That is, the pressure sensor 54 may be able to detect pressure amounts in the defect site 30, and in the osteochondral plugs 50 and 52, within a range of about 5 cm in any radial direction from the pressure sensor 54.

Figure 6F:
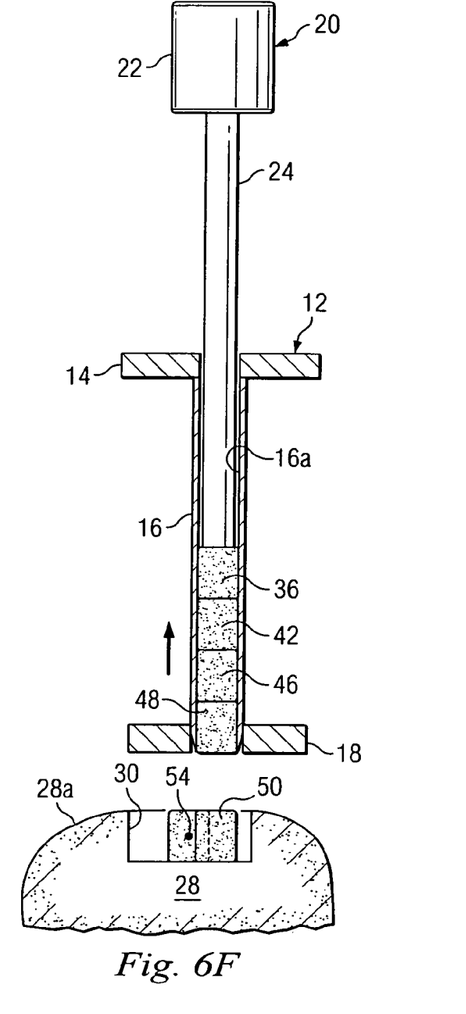

Referring to FIG. 6F, after the osteochondral plug 50 has been impacted into the defect site 30, the cannula 12 and the pusher device 20 are both lifted upwards and away from the defect site 30. During this movement, the osteochondral plugs 36, 42, 46 and 48 remain positioned in the tubular member 16, but the protrusion 24 does not apply an appreciable force against the osteochondral plug 36. In an exemplary embodiment, after the osteochondral plug 50 has been impacted into the defect site 30, the protrusion 24 of the pusher device 20 may be removed from the passage 16a of the tubular member 16 of the cannula 12.

Figure 6G:
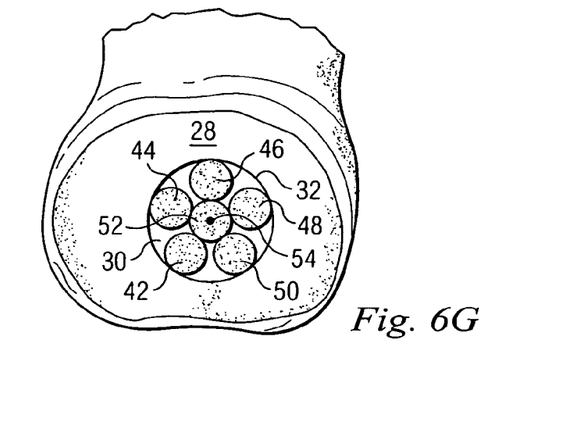
FIG. 6G is a top plan view of the osteochondral plugs of FIG. 5, after the osteochondral plugs have been impacted into the articular cartilage defect site of FIGS. 3A, 3B, 3C and 3D, using the apparatus of FIGS. 1A and 1B.

Referring to FIG. 6G, the osteochondral plugs 48, 46, 42 and 36 are each impacted into the defect site 30, and are each positioned adjacent the osteochondral plug 52, contacting or nearly contacting the osteochondral plug 52, in a manner substantially identical to the manner in which the osteochondral plug 50 is impacted into the defect site 30. During the impacting of each of the osteochondral plugs 48, 46, 42 and 36, the pressure sensor 54 measures the amount of pressure that the respective plug undergoes during its impacting into the defect site 30, in a manner substantially identical to the manner in which the pressure sensor 54 measures the amount of pressure that the osteochondral plug 50 undergoes during its impacting into the defect site 30.

As a result of the above-described impacting of the osteochondral plugs 52, 50, 48, 46, 42 and 36 into the defect site 30, the articular cartilage 28 is at least partially repaired. In several exemplary embodiments, the cannula 12 is used to both extract and impact the osteochondral plugs 52, 50, 48, 46, 42 and 36. Moreover, in several exemplary embodiments, since all of the osteochondral plugs 52, 50, 48, 46, 42 and 36 are positioned in the tubular member 16 prior to any impacting, the cannula 12 does not have to return to any donor sites after being positioned in the vicinity of the defect site 30.

Figure 7A:
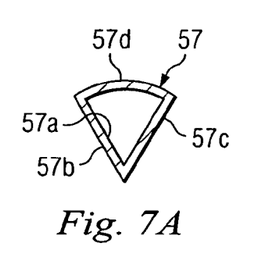
FIG. 7A is a sectional view of a cannula according to another embodiment.
Figure 7B:
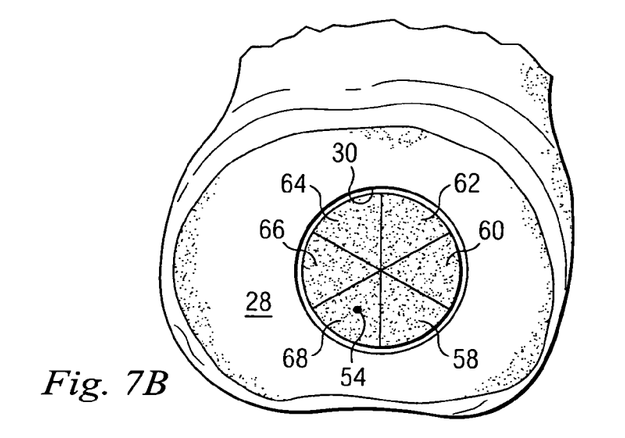
FIG. 7B is a top plan view of a plurality of osteochondral plugs, after the osteochondral plugs have been impacted into an articular cartilage defect site, using the cannula of FIG. 7A.

Referring to FIGS. 7A and 7B, instead of the tubular member 16, the cannula 12 may include an alternate tubular member 57 defining a longitudinal passage 57*a* including a generally slice-of-pie-shaped cross-section. That is, the cross-section of the tubular member 57 includes walls 57*b* and 57*c*, respective ends of which meet at a common vertex, and a curved, circumferentially-extending wall 57*d* extending between respective other ends of the walls 57*b* and 57*c*.

In operation, the alternate tubular member 57 may be used to extract and impact osteochondral plugs 58, 60, 62, 64, 66 and 68 into the defect site 30, with each of the osteochondral plugs being generally slice-of-pie shaped, that is, generally corresponding to the generally slice-of-pie-shaped cross-section of the passage 57*a*. The osteochondral plugs 58, 60, 62, 64, 66 and 68 may be extracted and impacted into the defect site 30 in a manner substantially similar to the above-described manner in which the osteochondral plugs 36, 42, 46, 48, 50 and 52 are extracted and impacted. The pressure sensor 54 is coupled to the osteochondral plug 68 so that the amount of pressure that each of the osteochondral plugs 58, 60, 62, 64, 66 and 68 undergoes during the impacting may be measured.

As a result of the generally slice-of-pie-shaped cross-section of the osteochondral plug 58, an increased amount of the external surface area of the osteochondral plug 58 engages the immediately adjacent osteochondral plugs 60 and 68. Likewise, an increased amount of the external surface area of each of the remaining osteochondral plugs 60, 62, 64, 66 and 68 engages the osteochondral plugs immediately adjacent thereto. Also, the quantity and sizes of any gaps between and among the osteochondral plugs 58, 60, 62, 64, 66 and 68, and the defect site 30, are minimized. As a result, any short or long-term bonding among the osteochondral plugs 58, 60, 62, 64, 66 and 68 may be strengthened or improved, and/or bonding may be initiated, and/or the repair of the defect site 30 may be facilitated.

Figure 8A:
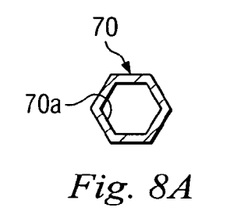
FIG. 8A is a sectional view of a cannula according to another embodiment.
Figure 8B:
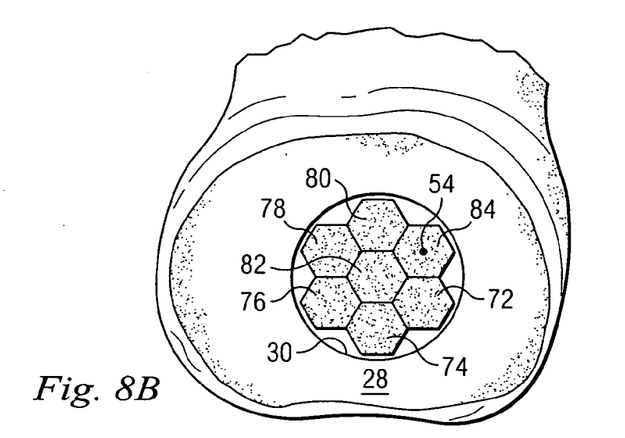
FIG. 8B is a top plan view of a plurality of osteochondral plugs, after the osteochondral plugs have been impacted into an articular cartilage defect site, using the cannula of FIG. 8A.

Referring to FIGS. 8A and 8B, instead of the tubular member 16, the cannula 12 may include an alternate tubular member 70 defining a longitudinal passage 70*a* including a generally hexagonal cross-section. In operation, the alternate tubular member 70 may be used to extract and impact osteochondral plugs 72, 74, 76, 78, 80, 82 and 84 into the defect site 30, with each of the osteochondral plugs having a hexagonal cross-section that generally corresponds to the generally hexagonal cross-section of the passage 70*a*. The osteochondral plugs 72, 74, 76, 78, 80, 82 and 84 may be extracted and impacted into the defect site 30 in a manner substantially similar to the above-described manner in which the osteochondral plugs 36, 42, 46, 48, 50 and 52 are extracted and impacted. The pressure sensor 54 is coupled to the osteochondral plug 84 so that the amount of pressure that each of the osteochondral plugs 72, 74, 76, 78, 80, 82 and 84 undergoes during the impacting may be measured.

As a result of the generally hexagonal cross-sections of the osteochondral plugs 72, 74, 76, 78, 80, 82 and 84, an increased amount of the external surface area of each of the osteochondral plugs 72, 74, 76, 78, 80, 82 and 84 engages the osteochondral plugs immediately adjacent thereto. Also, the quantity and sizes of any gaps between and among the osteochondral plugs 72, 74, 76, 78, 80, 82 and 84, and the defect site 30, are minimized. As a result, any short or long-term bonding among the osteochondral plugs 72, 74, 76, 78, 80, 82 and 84 may be strengthened or improved, and/or bonding may be initiated, and/or the repair of the defect site 30 may be facilitated.

Figure 9A:
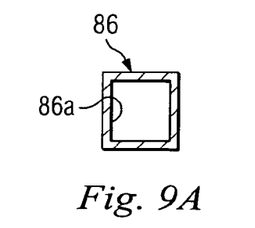
FIG. 9A is a sectional view of a cannula according to another embodiment.
Figure 9B:
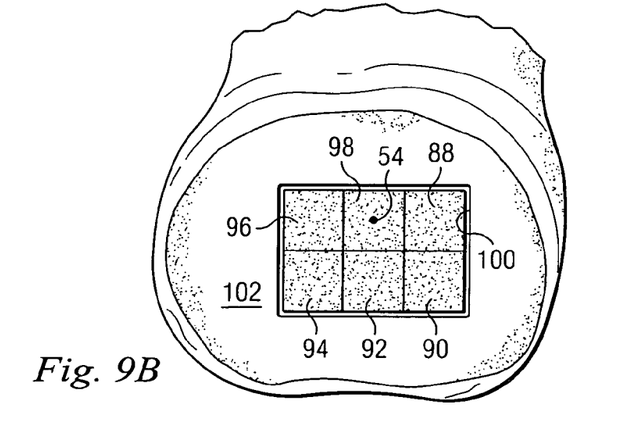
FIG. 9B is a top plan view of a plurality of osteochondral plugs, after the osteochondral plugs have been impacted into an articular cartilage defect site, using the cannula of FIG. 9A.

Referring to FIGS. 9A and 9B, instead of the tubular member 16, the cannula 12 may include an alternate tubular member 86 defining a longitudinal passage 86*a* including a generally square cross-section. In operation, the alternate tubular member 86 may be used to extract and impact osteochondral plugs 88, 90, 92, 94, 96 and 98 into a rectangular defect site 100 in articular cartilage 102, with each of the osteochondral plugs having a square cross-section that generally corresponds to the generally square cross-section of the passage 86*a*. The osteochondral plugs 88, 90, 92, 94, 96 and 98 may be extracted and impacted into the defect site 100 in a manner substantially similar to the above-described manner in which the osteochondral plugs 36, 42, 46, 48, 50 and 52 are extracted and impacted into the defect site 100. The pressure sensor 54 is coupled to the osteochondral plug 98 so that the amount of pressure that each of the osteochondral plugs 88, 90, 92, 94, 96 and 98 undergoes during the impacting may be measured.

As a result of the generally square cross-sections of the osteochondral plugs 88, 90, 92, 94, 96 and 98, an increased amount of the external surface area of each of the osteochondral plugs 88, 90, 92, 94, 96 and 98 engages the osteochondral plugs immediately adjacent thereto. Also, the quantity and sizes of any gaps between and among the osteochondral plugs 88, 90, 92, 94, 96 and 98, and the defect site 100, are minimized. As a result, any short or long-term bonding among the osteochondral plugs 88, 90, 92, 94, 96 and 98 may be strengthened or improved, and/or bonding may be initiated, and/or the repair of the defect site 100 may be facilitated.

VARIATIONS

It is understood that variations may be made in the foregoing without departing from the scope of the disclosure. For example, any of the osteochondral plugs may be in the form of an allograft, an autograft, a composite plug having polyactide-coglycolide, calcium sulfate and/or polyglycolide fibers, other types of composite plugs and/or any combination thereof. Also, one or more portions of the tubular members 16, 57, 70 and 86 may be transparent or at least partially transparent, or may include a window portion to provide at least partial transparency. Moreover, in addition to, or instead of the foregoing, the pressure sensor 54 may be in the form of a wide variety of other pressure sensors, which may include a wide variety of transducers and/or a wide variety of micro-electro-mechanical systems (MEMs). Also, the pressure sensor 54 may be coupled to any of the above-described osteochondral plugs such as, for example, the osteochondral plug 52, before the osteochondral plug 52 is extracted. That is, the pressure sensor may be coupled to the material of the donor site 34, of which the osteochondral plug 52 is composed, prior to the extraction of the osteochondral plug 52. Further, the pressure sensor 54, and/or one or more pressure sensors that are similar to the pressure sensor 54, may be coupled to any one of the above-described osteochondral plugs.

Still further, the sizes, dimensions and cross-sections of the above-described tubular members 16, 57, 70 and 86, and/or of the above-described osteochondral plugs, may be varied. For example, the diameter of one or more of the osteochondral plugs 36, 42, 46, 48, 50 and 52 may be 5 mm, 8 mm or 11 mm. For another example, the osteochondral plugs 36, 42, 46, 48, 50 and 52 may have rectangular, triangular, star-shaped or octagonal cross-sections. Also, osteochondral plugs of different sizes and shapes may be impacted into the same defect site such as, for example, the defect site 30 or 102. Moreover, the length of the tubular member 16, 57, 70 or 86 may be increased or decreased so that number of osteochondral plugs that may be positioned within the tubular member at the same time may be increased or decreased, respectively.

In an exemplary embodiment, an automatic feedback control system may be added to the apparatus 10, using the pressure measurement provided by the pressure sensor 54 as a feedback control signal, so that the amount of force applied by the protrusion 24 may be automatically adjusted in response to the pressure measurement provided by the pressure sensor 54.

Any spatial references such as, for example, "upper," "lower," "above," "below," "between," "vertical," "angular," "upwards," "downwards," "side-to-side," "left-to-right," "right-to-left," "top-to-bottom," "bottom-to-top," etc., are for the purpose of illustration only and do not limit the specific orientation or location of the structure described above.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several exemplary embodiments have been described in detail above, those skilled in the art will readily appreciate that many other modifications, changes and/or substitutions are possible in the exemplary embodiments without materially departing from the novel teachings and advantages of the present invention. Accordingly, all such modifications, changes and/or substitutions are intended to be included within the scope of this invention as defined in the following claims. In the claims, any means-plus-function clauses are intended to cover the structures described herein as performing the recited function and not only structural equivalents, but also equivalent structures.

What is claimed is:

1. A surgical apparatus comprising:
a transparent tubular member having a proximal end, distal end and an outer surface, said distal end including an adjustable stop extending laterally from the outer surface and configured to be moveable upwards or downwards relative to the tubular member, said stop being disposed relative to the distal end so that a distance between the stop and the distal end defines a height of an osteochondral plug, said stop configured to be fixed relative to said tubular member by one or more set screws, said tubular member defining a longitudinal passage configured for simultaneous disposal of a plurality of osteochondral plugs in axial alignment, the plurality of osteochondral plugs including an osteochondral plug and at least one other osteochondral plug disposed distally to the osteochondral plug;
a protrusion adapted to at least partially extend within the longitudinal passage of the tubular member; and
a pressure sensor adapted to be coupled to the at least one other osteochondral plug so that the at least one other osteochondral plug and the pressure sensor are positioned within the longitudinal passage of the tubular member at the same time.

2. The apparatus of claim 1 wherein the pressure sensor is adapted to measure a pressure associated with a force applied to the osteochondral plug via the protrusion wherein the pressure sensor is configured to detect pressure amounts within a range of 5 cm in any radial direction from the pressure sensor.

3. The apparatus of claim 2 further comprising a receiver in communication with the pressure sensor.

4. The apparatus of claim 3 wherein the pressure sensor is adapted to transmit a signal to the receiver, the signal corresponding to the pressure associated with the force.

5. The apparatus of claim 1 wherein the tubular member is adapted to be punched into a donor site; and
wherein the tubular member comprises a tapered distal end portion for facilitating the punching of the tubular member into the donor site.

6. The apparatus of claim 1 wherein the tubular member comprises a generally slice-of-pie-shaped cross-section.

7. The apparatus of claim 1 wherein the tubular member comprises a cross-section selected from the group consisting of a circular cross-section, a square cross-section, a rectangular cross-section, an octagonal cross-section and a hexagonal cross-section.

8. The apparatus of claim 1 wherein the pressure sensor includes a capacitor having a pair of spaced plates and a resonant frequency, the pressure sensor configured such that the resonant frequency is dependent upon the spacing between the plates of the sensor.

9. A surgical apparatus comprising:
a transparent tubular member having a proximal end, a distal end and an outer surface, said distal end including a stop comprising an adjustable clamp extending about the tubular member, said stop configured to be moveable upwards or downwards relative to the tubular member, said stop being disposed relative to the distal end so that a distance between the stop and the distal end defines a height of an osteochondral plug, wherein the stop is configured to be fixed relative to said tubular member by said adjustable clamp, said tubular member configured to receive and hold simultaneously a plurality of osteochondral plugs in alignment, the plurality of osteochondral plugs including a first osteochondral plug and at least one other osteochondral plug visible through said transparent tubular member, wherein the tubular member comprises a generally slice-of-pie-shaped cross-section; and
a protrusion adapted to be received by the tubular member;
wherein the apparatus comprises a first configuration in which:
the first osteochondral plug is received and held in place within the tubular member; and
the least one other osteochondral plug is received and held simultaneously in place within the tubular member in alignment with the first osteochondral plug; and
wherein the apparatus comprises a second configuration in which the protrusion is configured to engage the first osteochondral plug such that the at least one other osteochondral plug exits the tubular member.

10. The apparatus of claim 9 wherein the tubular member is adapted to be punched into a donor site to receive the first osteochondral plug; and
wherein the tubular member comprises a tapered distal end portion for facilitating the punching of the tubular member into the donor site.

11. The apparatus of claim 9 further comprising a pressure sensor configured to be coupled to the at least one other osteochondral plug so that the pressure sensor is positioned within the tubular member when the apparatus is in the first configuration.

12. The apparatus of claim 9 further comprising a pressure sensor configured to be coupled to the at least one other osteochondral plug so that the pressure sensor is positioned within the tubular member in the first configuration;
wherein, the second configuration of the apparatus allows for the at least one other osteochondral plug to be impacted into a defect site in response to a regulated application of force configured for application to the first osteochondral plug; and wherein the pressure sensor is configured to measure a pressure associated with the force during the impacting of the at least one other osteochondral plug into the defect site; and wherein the pressure sensor is configured to detect pressure amounts within a range of 5 cm in any radial direction from the pressure sensor.

13. The apparatus of claim 12 wherein said tubular member is configured to receive and hold six osteochondral plugs in alignment.

14. The apparatus of claim 13 wherein said osteochondral plugs have a height of 15 mm.

15. The apparatus of claim 12 wherein the pressure sensor includes a capacitor having a pair of spaced plates and a resonant frequency, the pressure sensor configured such that the resonant frequency is dependent upon the spacing between the plates of the sensor.

* * * * *